US009066755B1

(12) United States Patent
Jacobs et al.

(10) Patent No.: US 9,066,755 B1
(45) Date of Patent: Jun. 30, 2015

(54) NAVIGABLE DEVICE RECOGNITION SYSTEM

(71) Applicant: DePuy Synthes Products, Inc., Raynham, MA (US)

(72) Inventors: Scott Jacobs, Randolph, MA (US); Joshua Rodriguez, Howell, NJ (US); Hassan A. Serhan, South Easton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/106,371

(22) Filed: Dec. 13, 2013

(51) Int. Cl.
*G06F 19/00* (2011.01)
*G06Q 30/00* (2012.01)
*G06Q 90/00* (2006.01)
*A61B 19/00* (2006.01)

(52) U.S. Cl.
CPC .......... *A61B 19/5244* (2013.01); *A61B 19/5212* (2013.01); *A61B 19/44* (2013.01); *A61B 2019/5272* (2013.01); *A61B 2019/5257* (2013.01); *A61B 2019/442* (2013.01); *A61B 2019/446* (2013.01); *A61B 2019/448* (2013.01); *A61B 2019/5265* (2013.01); *A61B 2019/5274* (2013.01)

(58) Field of Classification Search
USPC .......................... 235/385, 375, 487
See application file for complete search history.

(56) References Cited

U.S. PATENT DOCUMENTS

| | | | |
|---|---|---|---|
| 2005/0228266 A1* | 10/2005 | McCombs | 600/414 |
| 2007/0136218 A1* | 6/2007 | Bauer et al. | 706/12 |
| 2008/0068197 A1* | 3/2008 | Neubauer et al. | 340/686.1 |
| 2009/0317002 A1* | 12/2009 | Dein | 382/224 |
| 2011/0208256 A1* | 8/2011 | Zuhars | 606/86 R |
| 2012/0136674 A1* | 5/2012 | Kreiner et al. | 705/2 |
| 2013/0345718 A1* | 12/2013 | Crawford et al. | 606/130 |

* cited by examiner

*Primary Examiner* — Edwyn Labaze
(74) *Attorney, Agent, or Firm* — Nutter McClennen & Fish LLP (57) ABSTRACT

Systems and methods for registering objects with a surgical navigation system are described herein. In one embodiment, a method for registering objects with a surgical navigation system can include detecting identification information associated with an object using a sensing device coupled to a digital data processor and detecting a position-tracking array using the sensing device. The method can also include searching a digital data store coupled to the digital data processor that contains a listing of objects and associated identification information to identify an object having identification information that matches the identification information detected by the sensing device, and registering with the surgical navigation system an association between the position-tracking array and the identified object.

25 Claims, 5 Drawing Sheets

NAVIGABLE DEVICE RECOGNITION SYSTEM

FIELD

The present invention relates to systems and methods for use in surgical procedures and, in particular, to systems and methods for registering objects with a surgical navigation system.

BACKGROUND

Surgical navigation systems allow for the precise tracking of instruments, implants, or other objects within an operating environment. To provide such precise tracking, surgical navigation systems typically employ a computer coupled to a set of stereoscopic infrared cameras that are positioned within the operating environment. Position-tracking arrays, which include a plurality of reflective members arranged in a unique geometry, are attached to each surgical instrument, implant, or other object to be tracked, and a calibration procedure is performed to establish a relationship between the orientation of the instrument and the array. A similar procedure is also performed to determine the position and orientation of the patient.

Once these calibration procedures are conducted, the surgical navigation system can compute the position and orientation of any tracked object based on the position and orientation of the associated array that is detected by the stereoscopic cameras. Further, the precise position of an object relative to the patient can be displayed to a surgeon or other user. Surgeons can then precisely navigate their instruments, implants, or other tools to perform the operation.

One problem often encountered when using a surgical navigation system is the need to exchange instruments between position-tracking arrays throughout the course of an operation. This is due to the fact that there are often fewer position-tracking arrays than instruments needed for an operation. Exchanging instruments between the position-tracking arrays is a time-consuming process that can require associating the new instrument with the array and calibrating the navigation system to use the correct orientation between the array and the instrument. In current surgical navigation systems these are manual processes that have a number of drawbacks. For example, there is a significant possibility for input or other user error in associating and/or calibrating instruments and position-tracking arrays. In addition, significant time is added to an operation to perform these procedures. Still further, surgeons or attendants may have to repeatedly leave or otherwise disturb a sterile field established in an operating environment in order to perform these procedures (e.g., by using a computer outside the sterile field, etc.), thereby increasing risk of infection or other complications. In response, surgeons may in some cases elect not to use the surgical navigation system for some instruments due to the inconvenience of the association and/or calibration procedures.

Accordingly, there is a need for improved systems and methods for identifying and registering surgical instruments, implants, and other objects for use with a surgical navigation system. In particular, there is a need for systems and methods for registering objects with a surgical navigation system that reduces the possibility for error and maintains the sterile field of an operating environment.

SUMMARY

The present invention generally provides systems and methods for recognizing and registering objects with a surgical navigation system. The systems and methods disclosed herein allow a user within an operating environment to efficiently and accurately register an instrument or other object for use with a surgical navigation system without disturbing a sterile field within the operating environment. Registration can be accomplished by detecting identification information associated with the instrument or object, as well as an associated position-tracking array. The detected identification information associated with the instrument or object can be compared to a listing of known instruments or objects and their associated identification information to determine a match, and once a match is located an association between the position-tracking array and the identified instrument or object can be registered with the surgical navigation system. Calibration data can also be loaded from a stored listing, or can be quickly detected based on image analysis in combination with known dimensions of the position-tracking array and identified instrument or object. In some embodiments, safety features can be included to inform a user of the identified instrument, or to inform of an inability to identify a matching instrument, as well as to require user confirmation prior to registration of the instrument with the surgical navigation system. A number of different techniques for detecting the position-tracking array and the identification information for the instrument or object are also provided, including, for example, analysis of visible-light images to recognize device shapes, detect surface markings (e.g., barcodes), etc., as well as other technologies such as radio-frequency identification (RFID) tags.

In one aspect, a surgical device recognition system includes a surgical device having an associated device identifier and a position-tracking array configured to mate to the surgical device. The system also includes a digital data processor configured to detect the device identifier associated with the surgical device using a sensing device coupled to the digital data processor and to detect the position-tracking array associated with the surgical device using the sensing device. The digital data processor is further configured to search a listing of surgical devices and associated device identifiers stored in a digital data store to identify a surgical device having a device identifier that matches the detected device identifier, and register with a surgical navigation system an association between the detected position-tracking array and the identified surgical device.

The systems and methods disclosed herein can have a number of additional features and/or variations, all of which are within the scope of the present invention. For example, a number of different sensing devices can be used in combination with the systems and methods disclosed herein. In one embodiment, the sensing device can include a visible-light camera and the digital data processor can be configured to detect the position-tracking array by analyzing an image of the position-tracking array captured by the sensing device. In other embodiments, however, the sensing device can include, for example, a radio frequency identification (RFID) tag reader, an optical barcode scanner, an infrared camera, or any other known sensing device.

Accordingly, in some embodiments, the device identifier associated with the surgical device can be encoded in a marking on an outer surface of the device. Similarly, the position-tracking array can include a marking on an outer surface thereof. The markings on the surgical device and/or the position-tracking array can be etched, engraved, printed, or otherwise formed in an outer surface of the device and/or array. Such markings can be permanently formed on an outer surface, or selectively attached to a device and/or array using, e.g., a detachable plate or tag. The markings on the device and/or the position-tracking array can, in some embodiments, be selected from the group consisting of a shape, a pattern, a one-dimensional barcode, and a two-dimensional barcode (e.g., a QR code). Information encoded in or associated with such markings can be read by means of image analysis to recognize shapes and/or patterns, oscillating directional light scanners (i.e., barcode scanners), or other known means of detection.

In still other embodiments, the device identifier can be encoded in a radio frequency identification (RFID) tag coupled to the surgical device. Similarly, the position-tracking array can include a radio-frequency identification tag coupled thereto that has identification information encoded therein. In such an embodiment, the digital data processor can be configured to read information encoded in the RFID tag or the device and/or array using a sensing device that includes an RFID sensor. The sensing device can be configured to read the information encoded in the RFID tags of the device and/or position-tracking array serially or simultaneously upon being placed within the field of view of the sensing device. As with the markings described above, an RFID tag can be permanently affixed to the device and/or position-tracking array, or selectively coupled thereto in any known manner.

It should be noted that in certain embodiments the position-tracking array may not include any marking, tag, or other component having information encoded therein. Rather, in these embodiments, the unique shape of the position-tracking array can be utilized to detect the position-tracking array without the need for any further identifying features. This can be accomplished using, e.g., a visible light image of the position-tracking array or infrared images captured by the surgical navigation system. In certain other embodiments, a device identifier can be similarly detected by recognizing a unique profile or shape of a device. In still other embodiments, a device identifier for a given device can be detected by recognizing a unique shape of an object attached to the device.

The systems and methods disclosed herein can include additional safety features to guard against any errors in identifying a surgical device being used during a procedure. For example, in some embodiments the system can further include a user interface for communicating information, and the digital data processor can be configured to communicate the identified surgical device to a user. The user interface used to communicate the identified object to the user can have a variety of forms. For example, in some embodiments a visual display, such as a liquid crystal display (LCD), can be employed to show a picture of the identified device such that the user can confirm that the identified device matches the actual device. In other embodiments, an audio interface can be utilized, and an identifying name, model number, or other information could be read aloud to a user to confirm that the object has been correctly identified. In embodiments where a display or other interface equipment is needed to communicate the identified object to the user, the equipment can be positioned either inside or outside of a sterile field in an operating environment. If placed within the sterile field, the equipment can be appropriately prepared to operate within the field, e.g., a display can be covered by a clear plastic hood, etc.

In certain embodiments, the systems and methods disclosed herein can also require a confirmation from a user prior to registering an association between a surgical device and a position-tracking array. This can be an additional safety check on top of simply displaying the identified device. For example, the system can further include an input device and the digital data processor can be configured to receive a confirmation from the user via the input device prior to registering the association between the position-tracking array and the identified device. Exemplary input devices can include, e.g., keyboards, mice, touch screens, foot pedals, voice-detecting microphones, gesture-detecting cameras, etc. In certain embodiments, input devices that maintain sterility in an operating environment can be preferred. Examples include foot pedals, voice-detecting microphones, and gesture-detecting cameras. However, in some embodiments, other input devices (e.g., keyboards, mice, touch screens, etc.) can be appropriately prepared for use in a sterile field, e.g., with a clear plastic covering or other known techniques.

In still other embodiments, the digital data processor of the system can be further configured to communicate a warning to a user via the display if the listing of surgical devices and associated identifiers does not include a match for the detected device identifier. Such a warning can serve as an additional safety check to prevent errors in registering devices for use with the surgical navigation system. For example, if the sensing device is unable to read information encoded in a marking on the object and/or position-tracking array, or if an additional view of the object and/or position-tracking array is required to confirm an identification match. The warning can take a variety of forms, including, for example, a visual warning on a display or other user interface device, an audio warning, or other known type of warning. By way of example, a display could include a bright red box, background, or other display element to serve as a warning until an identifying object is located. At that time, the display could be switched to include a bright green display element to communicate to a user that an identifying object has been located with an acceptable level of confidence. In some embodiments, users can provide corrective information to resolve such a warning. For example, a user interface can allow a user to manually select or input a device for registration using a keypad, foot pedal, etc. In certain embodiments, a system can be configured for voice control, wherein a user can call out device identifying information that can be used by the system to register a device and a position tracking array.

In another aspect, a method for registering objects with a surgical navigation system includes detecting identification information associated with an object (e.g., a surgical instrument, implant, or other object utilized during an operation) using a sensing device that is coupled to a digital data processor. The method further includes detecting a position-tracking array using the sensing device, and searching a digital data store coupled to the digital data processor that contains a listing of objects and associated identification information to identify an object having identification information that matches the identification information detected by the sensing device. The method can also include registering with the surgical navigation system an association between the position-tracking array and the identified object.

The method for registering objects with a surgical navigation system can include any of the variations or additional features described above. For example, in some embodiments the object and the sensing device can be spaced a distance apart from one another. This can allow the sensing device to detect identification information associated with an object without contacting the object. Detection can be accomplished using any number of methods known in the art, including, e.g., radio frequency or other wireless communication methods, analysis of visible-light or other types of images, etc.

Avoiding contact between the sensing device and the object and/or position-tracking array can have a number of advantages. One such advantage is the ability to maintain sterility within an operating environment. In particular, in some embodiments, the sensing device can be positioned outside of a sterile field in an operating environment and the object (and/or position-tracking array) can be positioned inside the sterile field. Detecting identification information associated with the object and detecting the position-tracking array while they are in the sterile field and without the need for contact can aid in maintaining the integrity of the sterile field while allowing more efficient use of the surgical navigation system.

As described above, a number of different sensing devices can be used in combination with the systems and methods disclosed herein. In one embodiment, the sensing device can include a visible-light camera to capture images of the object and its associated identification information, as well as the position-tracking array. In such an embodiment, detecting identification information associated with an object and detecting a position-tracking array can include analyzing one or more images of the object and one or more images of the position-tracking array captured by the sensing device. For example, the sensing device can be configured to detect the identification information associated with the object and the position-tracking array serially using, e.g., separate images of each component, or simultaneously using a single image capturing both the object and the position-tracking array.

In other embodiments, however, the sensing device can include, for example, a radio frequency identification (RFID) tag reader, an optical barcode scanner, an infrared camera, or any other known sensing device. Accordingly, in some embodiments, the identification information associated with the object can be encoded in a marking on an outer surface of the object. Similarly, detecting the position-tracking array can include reading information encoded in a marking on an outer surface of the array. The markings on the object and/or the position-tracking array can be etched, engraved, printed, or otherwise formed in an outer surface of the object and/or array. Such markings can be permanently formed on an outer surface, or selectively attached to an object and/or array using, e.g., a detachable plate or tag. The markings on the object and/or the position-tracking array can, in some embodiments, be selected from the group consisting of a shape, a pattern, a one-dimensional barcode, and a two-dimensional barcode (e.g., a QR code). Information encoded in such markings can be read by means of image analysis to recognize shapes and/or patterns, oscillating directional light scanners (i.e., barcode scanners), or other known means of detection.

In still other embodiments, the identification information associated with the object can be encoded in a radio frequency identification (RFID) tag coupled to the object. Similarly, detecting the position-tracking array can include receiving information encoded in a radio-frequency identification tag coupled to the array. In such an embodiment, a sensing device including an RFID sensor can be configured to detect the information encoded in the RFID tags of the object and/or position-tracking array serially or simultaneously upon being placed within the field of view of the sensing device. As with the markings described above, an RFID tag can be permanently affixed to the object and/or position-tracking array, or selectively coupled thereto in any known manner.

As mentioned above, however, in some embodiments the position-tracking array may not include any marking, tag, or other component having information encoded therein. Rather, in these embodiments, the unique shape of the position-tracking array can be utilized to detect the position-tracking array without the need for any further identifying features. This can be accomplished using, e.g., a visible light image of the position-tracking array or infrared images captured by the surgical navigation system. This concept can also be applied to detecting identification information associated with an object in certain embodiments. For example, a unique profile or shape of an object, or a unique profile or shape of a second object coupled to the object, can be utilized to detect identification information associated with the object.

Similar to the system described above, in some embodiments the methods for registering objects with a surgical navigation system can further include communicating the identified object to a user via a user interface prior to registering the association between the position-tracking array and the identified object. The user interface used to communicate the identified object to the user can have a variety of forms. For example, in some embodiments a visual display can be employed to show a picture of the identified object such that the user can confirm the identified object matches the actual object. In other embodiments, an audio interface can be utilized to read identifying information to a user. In embodiments where a display or other interface equipment is needed to communicate the identified object to the user, the equipment can be positioned either inside or outside of a sterile field in the operating environment. If placed within the sterile field, the equipment can be appropriately prepared to operate within the field, e.g., a display can be covered by a clear plastic hood, etc. In other embodiments, however, alternative user interfaces can be employed, including, for example, a voice control user interface that reads aloud information to a user and detects commands vocalized by a user.

The systems and methods disclosed herein can also require a confirmation from a user prior to registering an association between an object and a position-tracking array. For example, the method described above can further include receiving a confirmation from the user via the user interface prior to registering the association between the position-tracking array and the identified object. In such an embodiment, the user interface can include an input device for a user to provide the confirmation indication. Exemplary input devices include, e.g., keyboards, mice, touch screens, foot pedals, voice-detecting microphones, gesture-detecting cameras, etc.

In still other embodiments, methods for registering objects with a surgical navigation system can further include communicating a warning to a user via a user interface if the identification information detected by the sensing device is not sufficient to identify a matching object from the listing in the digital data store. Such a warning can serve as an additional safety check to prevent errors in registering devices for use with the surgical navigation system. For example, if the sensing device is unable to read information encoded in a marking on the object and/or position-tracking array, or if an additional view of the object and/or position-tracking array is required to confirm an identification match. The warning can take a variety of forms, including, for example, a visual warning on a display or other user interface device, an audio warning, or other known type of warning. By way of example, a display could include a bright red box, background, or other display element to serve as a warning until an identifying object is located. At that time, the display could be switched to include a bright green display element to communicate to a user that an identifying object has been located with an acceptable level of confidence. In certain embodiments, corrective action from a user can be detected via a user interface to address the warning. For example, a user can specify an object being registered by selecting or inputting the object identification information using a keyboard, foot pedal, voice command, etc.

In some embodiments, the method can further include registering with the surgical navigation system an orientation of the identified object relative to the position-tracking array. Registering an orientation between an object and a position-tracking array can allow for more accurate tracking of the object by the surgical navigation system. Orientation information can be detected in a number of different manners. For example, in some embodiments, the orientation of the identified object can be determined based on a shape of an object. By way of further example, a visible light image of an object having a position-tracking array coupled thereto can be analyzed to determine the relative orientation of the object and the array. The particular shape and dimensions of both the array and the instrument can be stored in the digital data store, such that image analysis can be utilized after identifying the object in the image to determine the relative orientation of the object and the array.

In still other embodiments, the identification information associated with the object can include orientation information. For example, a surgical instrument or other object can include a plurality of markings positioned at various locations thereon. Each marking can serve to identify a particular portion of the device (e.g., a distal tip of the device, etc.). Accordingly, a sensing device can detect the plurality of markings, reference their meanings stored in the digital data store, and compare to the known geometry of the position-tracking array to determine the components' relative orientation.

In another aspect, a method for managing instruments being tracked by a surgical navigation system includes receiving from an image capture device an image of an instrument and a position-tracking array, where the image includes an identification marker associated with the instrument. The method further includes searching a digital data store containing a listing of instruments and associated identification markers to identify a surgical instrument with a matching identification marker, and registering with the surgical navigation system an association between the position-tracking array and the identified surgical instrument.

Any and all of the additional features or variations described above can be applied to any particular aspect or embodiment of the invention; the absence of explicit recitation of any particular combination is solely due to avoiding repetition in this summary.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention is generally directed to systems and methods for efficiently and accurately registering objects with a surgical navigation system. The systems and methods disclosed herein can have particular advantage over prior art methods in that rapid registration of an instrument or other object can be accomplished without requiring a user to disturb a sterile field in an operating environment (e.g., by leaving the sterile field, touching a non-sterile input device, etc.). In general, registration of an object can be accomplished by using a sensing device to detect identification information associated with the object, as well as to detect a unique position-tracking array coupled to or associated with the object. A listing of objects and their associated identification information can be searched to identify an object with identification information that matches the information detected by the sensing device. Once such a match is located, an association between the detected position-tracking array and the identified object can be registered with the surgical navigation system, thereby allowing the surgical navigation system to accurately track and display the object.

Figure 1:
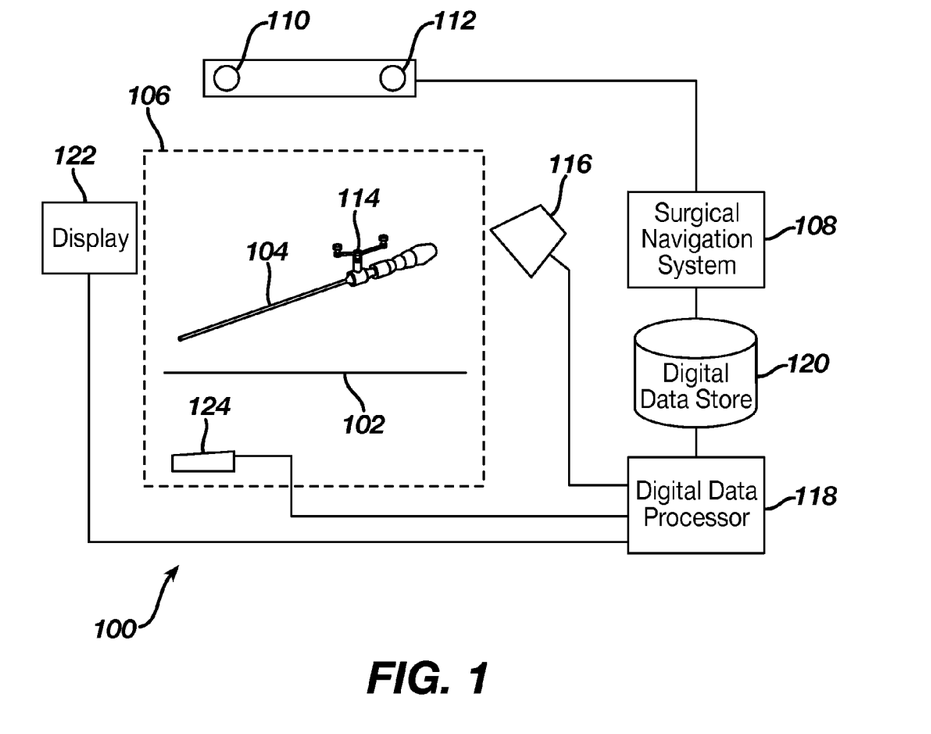
FIG. 1 is a diagram of one embodiment of a surgical device recognition system.

FIG. 1 illustrates one embodiment of a surgical device recognition system 100. The system 100 can be positioned in an operating environment, which can include an operating table 102 or other structure on which a patient can be placed, as well as one or more surgical instruments 104. The operating environment can include a sterile field 106 that encompasses the operating table 102, any surgical instruments 104, as well as the immediately surrounding area. A surgical navigation system 108 can be located within the operating environment as well. The surgical navigation system 108 can be embodied as software executing on a computer or other digital data processor to track surgical instruments 104 or other objects within the sterile field 106 of the operating environment. To do so, the surgical navigation system 108 includes a pair of stereoscopic cameras 110, 112 spaced a particular distance from one another and oriented to view the operating environment (e.g., above the operating environment as shown in the figure). In many embodiments, the stereoscopic cameras 110, 112 are infrared cameras that are able to detect reflections of infrared light from a plurality of reflective members that are disposed on position-tracking arrays 114 coupled to each surgical instrument 104.

Each position-tracking array 114 can have a unique geometry, i.e., a unique spatial arrangement of the plurality of reflective members disposed on the array. As a result, the stereoscopic cameras 110, 112 can identify each unique array, along with its orientation in space. The surgical navigation system 108 can use this information to compute the position and orientation of the surgical instrument 104 coupled thereto. This information can be combined with known data regarding a patient's position on the operating table 102 to provide a display of the precise location of the surgical instrument 104 (or any other object) relative to the patient's body.

As mentioned above, one common problem encountered when using a surgical navigation system is that there are fewer position-tracking arrays than there are instruments. In some cases, as few as about 6 position-tracking arrays may be available for use at any given time. As a result, position-tracking arrays such as the array 114 must be swapped among several different surgical instruments (e.g., instrument 104) or other objects that a surgeon desires to track. As described above, the process of manually swapping a position-tracking array among different instruments adds considerable time to an operation, has potential for input or other error from a user performing the swap, and often requires a user to exit or otherwise disturb the sterile field 106 of the operating environment.

In order to address these and other shortcomings of the prior art systems and methods for registering objects with a surgical navigation system, the system 100 can be provided with a sensing device 116 that is able to view objects within the sterile field 106. The sensing device 116 can be configured to detect identification information associated with an object, such as the surgical instrument 104. The sensing device 116 can also be configured to detect the unique position-tracking array 114 that is coupled to or otherwise associated with the surgical instrument 104. This information can be conveyed to a digital data processor 118 coupled to the sensing device 116.

The digital data processor 118 can be a dedicated hardware component (e.g., a computer) or it can be a dedicated processor or software integrated into the surgical navigation system 108. In any case, the digital data processor 118 can be coupled to a digital data store 120 that contains a listing of surgical objects and associated identification information for each object. The digital data store can also include other information related to each object, such as dimension and/or orientation information for use by the surgical navigation system in determining the position of the instrument based on the position of an associated array.

The digital data processor 118 can be configured to search the digital data store 120 to locate a matching object or instrument that has identical identification information to the information detected by the sensing device 116. If such a match is located, the digital data processor 118 can register with the surgical navigation system 108 an association between the identified object or instrument and the position-tracking array (e.g., an association between the instrument 104 and the position-tracking array 114). This association, in combination with the dimension and/or orientation information for the array 114 and instrument 104, can be utilized by the surgical navigation system 108 to determine the exact position of the instrument 104 based on the position of the array 114 detected by the stereoscopic cameras 110, 112.

In certain embodiments, the surgical device recognition system 100 can also include a user interface that includes any of a display 122 (e.g., a liquid crystal display, or LCD) and an input device 124 (e.g., a foot pedal). The components of the user interface can be coupled to the digital data processor such that an identified matching object or surgical instrument can be displayed to a user via the display 122. This can act as a safety feature to allow a user to ensure that there has been no error in identifying the device presented to the sensing device 116. In other embodiments, an additional safety feature can be implemented that requires a user to provide a confirmation notice via the input device 124 prior to registration of an association between the position-tracking array and the instrument or other object. Importantly, all interactions between a user and the digital data processor can be conducted without disturbing the sterile field 106. That is, the user does not have to leave the sterile field 106, and also can avoid touching any non-sterile equipment by using the foot pedal input device 124. Still further, the display 122 and sensing device 116 can, in some embodiments, be positioned outside the sterile field 106 as physical contact is not necessary for either component's operation. In other embodiments, the user interface can include voice control capabilities. An auditory input device (e.g., a microphone), can detect a user's vocalized commands and react accordingly. Similarly, an auditory speaker can be utilized in place of, or in addition to, the display 122 to communicate with a user.

The sensing device 116 can utilize a number of different technologies to provide detection of objects and position tracking arrays without requiring physical contact with the objects or arrays. For example, in some embodiments the sensing device 116 can be a visible light camera so that visible light images of various instruments or other objects can be collected and analyzed. Analysis of visible-light images can allow the sensing device 116 or digital data processor 118 to read identification information that is encoded in markings formed on an outer surface of an instrument 104 or array 114.

Figure 2:
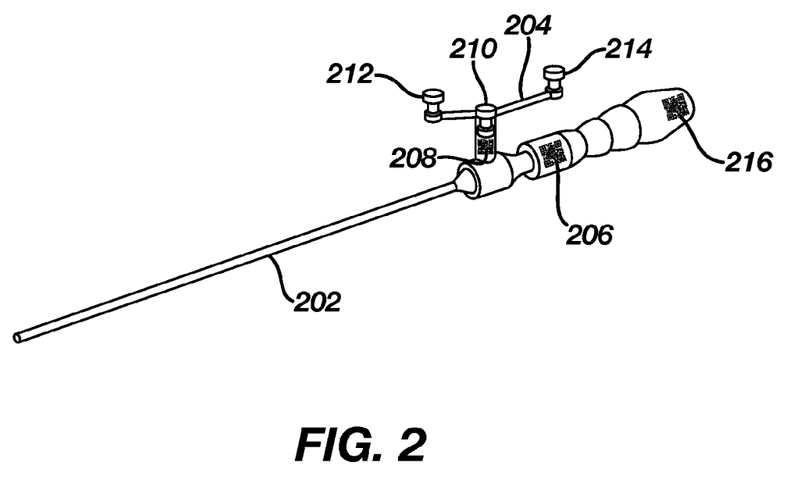
FIG. 2 is an illustration of one embodiment of a surgical instrument and position-tracking array.

FIG. 2 illustrates one embodiment of a surgical instrument 202 and a position-tracking array 204 that each include markings formed on an outer surface thereof. Surgical instrument 202, for example, includes a two-dimensional barcode 206 (e.g., a quick response, or QR, code) disposed on an outer surface thereof. The position-tracking array 204 also includes a two-dimensional barcode 208 disposed on an outer surface thereof. In such an embodiment, a visible light camera sensing device can capture an image of the instrument 202 and the position-tracking array 204 and read identification information for each component from the barcodes.

Note that in certain embodiments, the position-tracking array 204 need not include any marking 208 to provide identification information. This is because each position-tracking array 204 includes a plurality of reflective members 210, 212, 214 that have a unique geometry relative to one another. Accordingly, the position-tracking array 204 can be identified from a visible light image (or an infrared image if the sensing device 116 is interfaced with the stereoscopic cameras 110 and 112, or includes its own infrared cameras) without the need for further identifying markings.

The barcode 206 can include any of a variety of identification information encoded therein. For example, the barcode 206 can include a serial number of the instrument 202, or alternatively (or additionally) can include a model number, a unique-identification number, a version number, a designation of instrument size, a product name, etc. Any piece of information that can be used to identify the instrument 202 from a list of possible instruments stored in the digital data store 120 can be encoded in the marking formed on the outer surface of the instrument.

Figure 3A:
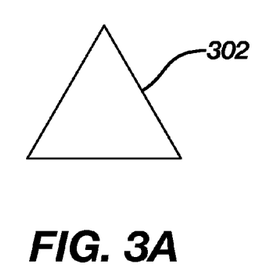
FIG. 3A is an illustration of one embodiment of an identification information marking in the form of a shape.
Figure 3B:
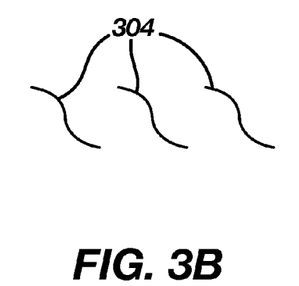
FIG. 3B is an illustration of an alternative embodiment of an identification information marking in the form of a pattern.
Figure 3C:
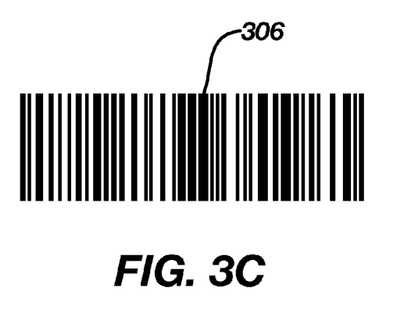
FIG. 3C is an illustration of an alternative embodiment of an identification information marking in the form of a one-dimensional barcode.
Figure 3D:
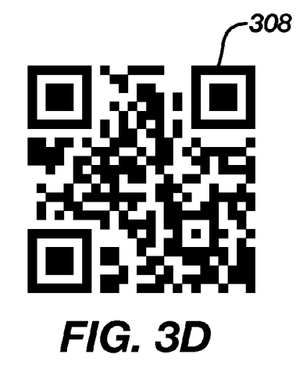
FIG. 3D is an illustration of an alternative embodiment of an identification information marking in the form of a two-dimensional barcode.

Furthermore, the markings 206, 208 themselves can have a variety of forms. For example, the markings 206, 208 can include a shape, such as the triangle 302 of FIG. 3A, or a combination of several shapes (e.g., squares, circles, etc.). In other embodiments, the markings 206, 208 can include a pattern of repeating shapes or lines, such as the repeating sequence of curved lines 304 shown in FIG. 3B (or other shapes such as grooves, etc.). In still other embodiments, a one-dimensional barcode can be employed, such as the barcode 306 shown in FIG. 3C. FIG. 3D shows an enlarged representation of a two-dimensional barcode 308, similar to the two-dimensional barcodes illustrated in FIG. 2.

In certain embodiments it can be possible to use alternative methods of communicating identification information between a position-tracking array, surgical instrument or other object, and the sensing device 116. For example, in some embodiments radio-frequency identification (RFID) tags can be used to encode identification information and communicate it to the surgical device recognition system 100.

Figure 4:
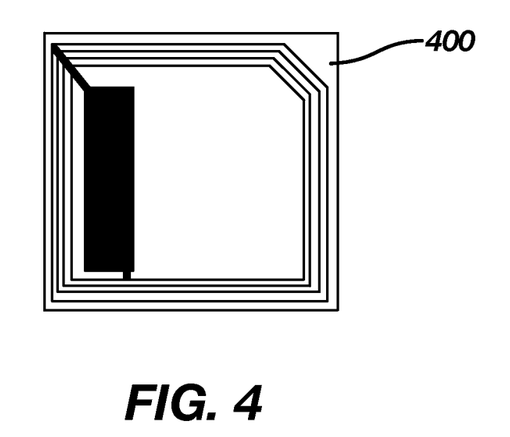
FIG. 4 is an illustration of one embodiment of a radio-frequency identification (RFID) tag containing identification information.

An exemplary RFID tag 400 is shown in FIG. 4. RFID tags come in a variety of shapes and sizes, and can be easily affixed to a variety of instruments using adhesives or other known attachment techniques. In such an embodiment, sensing device 116 can include an RFID tag reader that is able to detect and read information encoded in an RFID tag placed in its view. In certain embodiments, a sensing device can include both a visible light camera and an RFID tag reader such that identification information can be read from the RFID tag affixed to the instrument and/or position-tracking array, but orientation information (e.g., the particular orientation of the position-tracking array in space) can be gathered from visible-light image analysis.

Figure 2A:
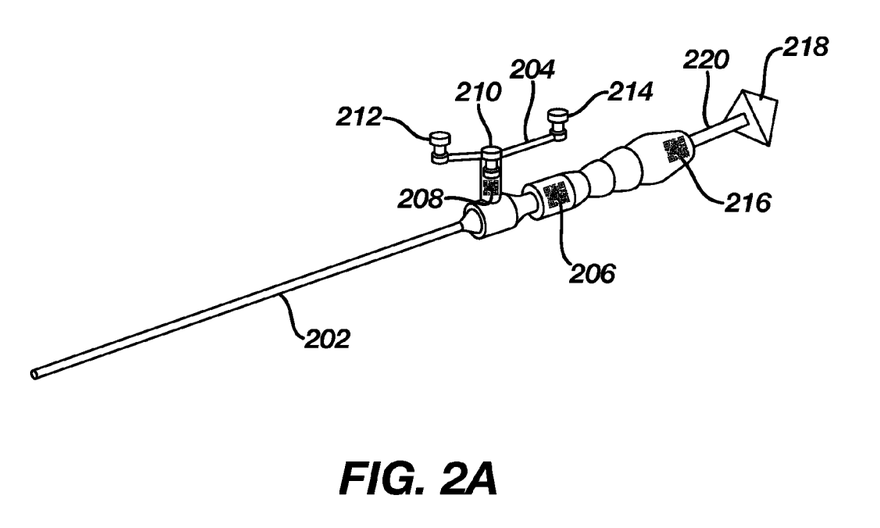
FIG. 2A is an illustration of an alternative embodiment of a surgical instrument including one embodiment of an identification marker.

In still other embodiments, an separate identification marker can be coupled to the surgical instrument 202 to provide identifying information. For example, and as shown in FIG. 2A, an identification marker 218 can be coupled to the surgical instrument 202. The identification marker 218 can have a unique shape (e.g., a pyramid as shown, though any shape can be used) that can be recognized by a sensing device. The identification marker 218 can be coupled to the surgical instrument 202 in a variety of manners. For example, in some embodiments the marker 218 can be coupled to the instrument 202 via a clamp, band, or other known attachment mechanism. In the illustrated embodiment, for example, a threaded bore on the surgical instrument 202 can accept a threaded shaft 220 that extends from the marker 218.

Utilizing separate identification markers (e.g., marker 218) can provide an advantage in that the system can be used with surgical devices that do not include identifying markings, as described above. In such a scenario, a surgical device need only be capable of coupling to an identification marker to be used with the system. In such a case, a user can enter an association between a particular identification marker (e.g., a marker shaped as a cube, pyramid, etc.) and the instrument it is coupled to, thereby allowing the instrument to be recognized and associated with a position tracking array.

Methods of using the various embodiments of the surgical device recognition system 100 described above are also provided herein. In one embodiment, for example, a method for registering objects with a surgical navigation system can include detecting identification information associated with an object using a sensing device. The identification information can be detected by the sensing device in a variety of manners, including through image analysis of visible light images captured by the sensing device (e.g., to read information encoded in markings on the object or recognize a unique shape of a device or object coupled to the device) or by reading an RFID tag having identification information encoded thereon.

The method can also include detecting a position-tracking array using the sensing device. The position-tracking array can be detected by the sensing device in the same manner as the identification information for the object to be tracked. That is, image analysis of visible-light images can be conducted to read markings formed on the array or information can be read from an RFID tag affixed to the array. In other embodiments, however, image analysis of the unique geometry of the position-tracking array can result in detection without the need for any further markings, RFID tags, etc.

In addition, detecting the identification information associated with the object and detecting the position-tracking array can be conducted simultaneously or serially. For example, in some embodiments a single image can be captured of the object and the position-tracking array coupled thereto. Image analysis can be conducted on the single image to extract the identification information and identify the position-tracking array. In other embodiments, however, an image of an object can be captured followed by an image of a position-tracking array, or vice-versa. Note that an additional image of the array assembled to the instrument can be necessary if the exact orientation between the two components is not known in advance.

After detecting the identification information associated with the object to be tracked, the method can include searching a digital data store containing a listing of objects and associated identification information to identify an object having identification information that matches the identification information detected by the sensing device. In other words, the detected identification information can be used as a query to locate a matching object in the listing. A matching entry in the listing can also include additional information, such as dimension or orientation information, as described in more detail below.

If a matching object is located, the method can include registering with the surgical navigation system an association between the position-tracking array and the identified object. The association can be used by the surgical navigation system to precisely track the movements of the identified object based on the movements of the associated position-tracking array.

In some embodiments, the method can include additional steps designed to provide enhanced safety against errors in associating objects with arrays. For example, in some embodiments the method can include communicating the identified object to a user via a user interface prior to registering the association between the position-tracking array and the identified object. The identified object can be communicated to a user in a variety of manners. For example, and as discussed above, communication can be by way of the display 122 that is part of the user interface of system 100. In particular, an image of the identified object, possibly along with identification information (e.g., name, model number, description, etc.), can be displayed to a user. In other embodiments, however, an auditory user interface can be employed wherein a voice reads identification information to a user. Communicating the identified object to the user in this manner can provide the user an opportunity to check for error in identifying the object.

In other embodiments, the method can also include receiving a confirmation from the user via the user interface prior to registering the association between the position-tracking array and the identified object. By requiring a confirmation from the user, an additional layer of security is added to the method to safeguard against error and potential injury to a patient. Of note is that even though the user can be required to confirm the identification of the object prior to registration with the surgical navigation system, a user need not leave or otherwise disturb the sterile field 106 of the operating environment to provide the confirmation. Rather, a user can provide the confirmation using, for example, the foot pedal input device 124 shown in FIG. 1. Alternatively, other input devices can be utilized that allow for operation without disturbing the sterile field 106. Examples include motion recognition cameras, voice recognition microphones, sterile touch screen interfaces, and third party data inputters, among others. In some embodiments, these alternative user interfaces (e.g., voice control, motion control, etc.) can be utilized to provide complete control of the system. For example, in one embodiment a voice control system can allow a user to vocalize identifying information for a device, and the system can register an association between the detected position-tracking array and the device called out by the user.

In still other embodiments, the method can include communicating a warning to a user via the user interface (e.g., display 122) if the identification information detected by the sensing device is not sufficient to identify a matching object from the listing in the digital data store. The warning can alert a user to a complete inability to identify an object having matching identification information, or to a possible lack of confidence in a selection that is presented to a user. For example, if a partial match is found, the display 122 can include a flashing banner, color overlay, or other element to connote to a user that the match is partial and there is not a high degree of confidence in the selection. In certain embodiments, corrective actions taken by users to address any warning displayed or otherwise communicated to the user. For example, in certain embodiments a user can manually input or select a device being used in response to warning that no matching device has been detected. The manual input or selection can be accomplished using any other user interfaces described herein, including, for example, voice control, keypad control, etc.

In addition to associating a given instrument or object with a particular position-tracking array, the systems and methods disclosed herein can also convey information to aid in determining an orientation between the object and the array. Orientation information can be important to provide precise tracking information after the association is complete. For example, if an instrument can be coupled to a position-tracking array in a variety of manners (e.g., on a plurality of outer surfaces, etc.), information about the relative orientation of the array and the instrument can be necessary before accurate tracking can be provided.

Accordingly, in some embodiments the methods disclosed herein can include registering with the surgical navigation system an orientation of the identified object relative to the position-tracking array. This can be accomplished in a variety of manners. In certain embodiments, for example, the orientation of the identified object can be determined based on a shape of the object. FIG. 2, by way of further example, illustrates a surgical instrument 202 having a position-tracking array 204 attached thereto. If the array 204 can only be attached to the object at the point shown, then there are only two choices regarding the possible orientation of the instrument 202 relative to the array 204 (i.e., the tapered end can extend to the left as shown in the figure, or the tapered end can extend to the right). A sensing device, such as a visible light camera, can determine the direction that the tapered end of the instrument 204 is extending from a captured image and therefore determine the relative orientation of the instrument 202 and the array 204.

In other embodiments, however, the identification information associated with the object can include orientation information. Referring again to FIG. 2, the instrument 202 includes first marking 206 and a second marking 216. The second marking 216 can be encoded with information regarding the orientation of the device, e.g., a notation that the second marking 216 represents the proximal end of the device. This information can be used by the surgical navigation system to determine the relative orientation of the instrument 202 and the array 204.

Any number of markings can be provided to denote particular features or surfaces of an instrument that can be utilized in determining the relative orientation of the instrument and an array. For example, a curved probe (e.g., having a part number of 123.456) can include four angular positions uniquely identified by different markings (e.g., barcodes, numbers, shapes, patterns, etc.). In one embodiment, the markings can be the part number with an added suffix to denote the angular position being viewed, e.g., 123.456.1 for 0°, 123.456.2 for 90°, 123.456.3 for 180, and 123.456.4 for 270°. The listing in the digital data store 120 can include all of these identification numbers as if there were separate unique instruments. If the sensing device (e.g., device 116) can recognize a position-tracking array and any of the four angular markers in a captured image, association and orientation between the array and the instrument can be determined.

The use of markings having orientation information encoded therein can be particularly advantageous in embodiments where the markings and position-tracking arrays are stand alone components that can be applied to any device (e.g., in comparison to devices manufactured to include such markings and mounting points for coupling to an array). In such an embodiment, a user can affix a number of markings to a device that appropriately define the orientation of the device, and the position-tracking array can be attached to the device at any convenient location. The orientation of such a device relative to the position tracking array can then be determined by the system 100 in the same manner described above.

The systems and methods disclosed herein can also allow for additional calibration of the surgical navigation system with respect to paired instruments or other objects and position-tracking arrays. For example, a sensing device can be utilized to capture an image of an instrument and position-tracking array coupled together and placed next to a calibration object of known dimensions. Image analysis techniques can be performed in the digital data processor 118 to determine the exact dimensions of the instrument and/or array. If the dimensions of at least one of the instrument or array are already accurately stored in the digital data store 120, no additional calibration object is necessary to determine the dimensions of the unknown instrument or array. This technique can also be applied to the measurement of, for example, implants to be placed within a patient during a procedure. A known calibration object or position-tracking array can be coupled to or placed in proximity to an implant and an image captured by the sensing device 116 can be utilized to determine the dimensions of the implant.

The systems and methods described above provide a number of advantages over prior art methods for registering objects with a surgical navigation system. In particular, the systems and methods disclosed herein allow for the rapid and accurate registration of objects with the surgical navigation system without requiring a user to leave or otherwise disturb a sterile field in an operating environment. Equipment utilized in performing the recognition and registration process can be located outside the sterile field, but physical contact between the equipment and the devices or users within the sterile field is not necessary.

Furthermore, the systems and methods disclosed herein reduce the possibility of user error in inputting and associating an instrument or object with a position-tracking array for use with the surgical navigation system. Moreover, the methods disclosed for registering an association between an instrument and a position-tracking array can include additional safety features such as a display of an identified device and a corresponding confidence indication, as well as a requirement for user confirmation before storing an association.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A surgical device recognition system, comprising:
   a plurality of surgical devices each having an associated device identifier;
   a position-tracking array mated to a first surgical device and configured to mate to any of the plurality of surgical devices; and
   a digital data processor configured to:
      detect a first device identifier associated with the first surgical device using a sensing device coupled to the digital data processor;
      detect the position-tracking array mated to the first surgical device using the sensing device;
      search a listing of surgical devices and associated device identifiers stored in a digital data store to identify a surgical device having a device identifier that matches the detected first device identifier;
      register with a surgical navigation system an association between the detected position-tracking array and the identified first surgical device;
      detect a second device identifier associated with a second surgical device using the sensing device after the position-tracking array is mated to the second surgical device;
      search the listing of surgical devices and associated device identifiers to identify a surgical device having a device identifier that matches the detected second device identifier; and
      replace the association registered with the surgical navigation system with a second association between the position-tracking array and the identified second surgical device.

2. The system of claim 1, wherein the sensing device comprises a visible-light camera and the digital data processor is configured to detect the position-tracking array by analyzing an image of the position-tracking array captured by the sensing device.

3. The system of claim 1, wherein the first device identifier associated with the first surgical device is encoded in a marking on an outer surface of the device and the marking is selected from the group consisting of a shape, a pattern, a one-dimensional barcode, and a two-dimensional barcode.

4. The system of claim 1, wherein the position-tracking array includes a marking on an outer surface thereof and the marking is selected from the group consisting of a shape, a pattern, a one-dimensional barcode, and a two-dimensional barcode.

5. The system of claim 4, wherein the digital data processor is configured to detect the position-tracking array by reading information encoded in the marking.

6. The system of claim 1, wherein the first device identifier associated with the first surgical device is encoded in a radio-frequency identification (RFID) tag coupled to the surgical device.

7. The system of claim 1, further comprising a radio-frequency identification (RFID) tag coupled to the position-tracking array, wherein the digital data processor is configured to detect the position-tracking array by reading information encoded in the RFID tag.

8. The system of claim 1, further comprising a display, wherein the digital data processor is further configured to communicate the identified first surgical device to a user via the display.

9. The system of claim 8, further comprising an input device, wherein the digital data processor is further configured to receive a confirmation from the user via the input device prior to registering the association between the position-tracking array and the identified first surgical device.

10. The system of claim 8, wherein the digital data processor is further configured to communicate a warning to the user via the display if the listing of surgical devices and associated device identifiers does not include a match for the detected first device identifier.

11. A method for registering objects with a surgical navigation system, comprising:
   detecting first identification information associated with a first object using a sensing device that is coupled to a digital data processor;
   detecting a position-tracking array mated to the first object using the sensing device;
   searching a digital data store coupled to the digital data processor that contains a listing of objects and associated identification information to identify an object having identification information that matches the first identification information detected by the sensing device;
   registering with the surgical navigation system an association between the position-tracking array and the identified first object;
   detecting second identification information associated with a second object using the sensing device after the position-tracking array is mated to the second object;
   searching the digital data store to identify an object having identification information that matches the second identification information detected by the sensing device; and
   replacing the association registered with the surgical navigation system with a second association between the position-tracking, array and the identified second object.

12. The method of claim 11, wherein the first object and the sensing device are spaced a distance apart from one another.

13. The method of claim 11, wherein the sensing device is positioned outside of a sterile field in an operating environment and the first object is positioned inside of the sterile field.

14. The method of claim 11, wherein the sensing device comprises a visible-light camera and detecting a position-tracking array comprises analyzing an image of the position-tracking array captured by the sensing device.

15. The method of claim 11, wherein the first identification information associated with the first object is encoded in a marking on an outer surface of the first object and the marking is selected from the group consisting of a shape, a pattern, a one-dimensional barcode, and a two-dimensional barcode.

16. The method of claim 11, wherein detecting the position-tracking array comprises reading information encoded in a marking on an outer surface of the array and the marking is selected from the group consisting of a shape, a pattern, a one-dimensional barcode, and a two-dimensional barcode.

17. The method of claim 11, wherein the first identification information associated with the first object is encoded in a radio-frequency identification (RFID) tag coupled to the first object.

18. The method of claim 11, wherein detecting the position-tracking array comprises receiving information encoded in a radio-frequency identification (RFID) tag coupled to the array.

19. The method of claim 11, further comprising communicating the identified first object to a user via a user interface prior to registering the association between the position-tracking array and the identified first object.

20. The method of claim 19, further comprising receiving a confirmation from the user via the user interface prior to registering the association between the position-tracking array and the identified first object.

21. The method of claim 11, further comprising communicating a warning to a user via a user interface if the first identification information detected by the sensing device is not sufficient to identify a matching object from the listing in the digital data store.

22. The method of claim 11, further comprising registering with the surgical navigation system an orientation of the identified first object relative to the position-tracking array.

23. The method of claim 22, wherein the orientation of the identified first object is determined based on a shape of the first object.

24. The method of claim 22, wherein the first identification information associated with the first object includes orientation information.

25. A method for managing instruments being tracked by a surgical navigation system, comprising:
receiving from an image capture device an image of a first instrument and a position-tracking array mated to the first instrument, the image including a first identification marker associated with the first instrument;
searching a digital data store containing a listing of instruments and associated identification markers to identify a surgical instrument with a matching identification marker;
registering with the surgical navigation system an association between the position-tracking array and the identified first surgical instrument;
receiving from an image capture device a second image of a second instrument mated to the position-tracking array, the second image including a second identification marker associated with the second instrument;
searching the digital data store to identify a surgical instrument with a matching identification marker; and
replacing the association registered with the surgical navigation system with a second association between the position-tracking array and the identified second surgical instrument.

* * * * *